United States Patent [19]

Cone, Jr. et al.

[11] Patent Number: 4,481,298

[45] Date of Patent: Nov. 6, 1984

[54] PRE-PRECIPITATED DOUBLE ANTIBODY IMMUNOASSAY METHOD

[75] Inventors: Robert O. Cone, Jr.; Charles R. Carpenter, both of Seguin, Tex.

[73] Assignee: AMF Incorporated, White Plains, N.Y.

[21] Appl. No.: 351,153

[22] Filed: Feb. 19, 1982

Related U.S. Application Data

[63] Continuation-in-part of Ser. No. 253,659, Apr. 13, 1981, Pat. No.

[51] Int. Cl.$^3$ .................. G01N 33/54; G01N 33/78
[52] U.S. Cl. .................. 436/500; 436/512; 436/536; 436/540; 436/542; 436/804; 436/808; 436/809; 436/817; 435/7; 260/112 R
[58] Field of Search .................. 424/1, 1.5, 1.1, 85; 23/230 B; 436/536–542, 547, 500–503, 512, 513, 804, 808, 809, 811, 815, 817; 435/4, 7, 21; 260/112 R

[56] References Cited

U.S. PATENT DOCUMENTS

| | | | |
|---|---|---|---|
| 3,872,225 | 3/1975 | Coller et al. | 424/1 |
| 3,995,018 | 11/1976 | Sjoquist | 424/1.5 |
| 4,048,298 | 9/1977 | Niswender . | |
| 4,092,408 | 5/1978 | Litt . | |
| 4,106,907 | 8/1978 | Charlton et al. | 424/1 X |
| 4,141,687 | 2/1979 | Forrest et al. | 424/1 X |
| 4,166,106 | 8/1979 | Sedlácek et al. . | |
| 4,166,844 | 9/1979 | Tu . | |
| 4,189,466 | 2/1980 | Ainis et al. . | |
| 4,231,199 | 11/1980 | Carlsson et al. | 436/518 |
| 4,232,001 | 11/1980 | Jensen et al. | 424/1 |
| 4,232,119 | 11/1980 | Carlsson et al. | 436/512 |
| 4,239,743 | 12/1980 | Sedlacek et al. . | |
| 4,244,940 | 1/1981 | Jeong et al. | 436/500 |
| 4,271,140 | 6/1981 | Bunting | 436/500 |
| 4,273,756 | 6/1981 | Ling et al. | 424/1 |
| 4,292,296 | 9/1981 | Parsons, Jr. | 424/1 |
| 4,292,403 | 9/1981 | Duermeyer | 435/5 |
| 4,312,944 | 1/1982 | Mattiasson et al. | 435/7 |
| 4,332,783 | 6/1982 | Pernice et al. | 436/512 |

FOREIGN PATENT DOCUMENTS 1248764 of 1971 United Kingdom .

OTHER PUBLICATIONS

Smith, Journal of Immunoassay, 2 (1), 75–84 (1981).
Soto et al., Clinical Chemistry, 22 (7), 1186 (1976).
Brown et al., Clinical Chemistry, 26 (3), 1980, 503–507.
Ashby et al., Clinica Chimica Acta, 101 (1980) 293–297.
Wong et al., Preconjugated Double Antibody Method for Separating Bound and Free Antigen in Radioimmunoassay, Jan. 1980, pp. 52–57.
Chard, "An Introduction to Radioimmunoassay and Related Techniques", North-Holland Publishing Co., 1978, pp. 401–425.
Chemical Abstracts, 96: 48449n, 1982.
ZETA-T$_3$U Test Kit, T$_4$ Test Kit and DIG Test Kit, AMF Biological and Diagnostic Products Co., Seguin, Texas 78155 (Issued Jul. 1981).
Hudson L. et al., *Practical Immunology*, Blackwell Scientific Publication, Oxford, England, 1976, pp. 181–198.
Clinical Chemistry, vol. 22, (7), p. 1186 (1976), Soto et al.
Clinical Chemistry, vol. 26 (3), pp. 503–507 (1980), Brown et al.
Clinica Chimica Acta, vol. 101, pp. 293–297 (1980), Ashby et al.
Chemical Abstracts, vol. 96, p. 279, abstract #48449n, Wong et al.

*Primary Examiner*—Benjamin R. Padgett
*Assistant Examiner*—M. Moskowitz
*Attorney, Agent, or Firm*—David E. Dougherty; Michael E. Zall

[57] ABSTRACT

An immunoassay process for the detection of an antigen in a sample, which comprises: (a) forming a mixture of the sample with (1) a preformed complex of a primary antibody and a secondary binding macromolecule therefor, wherein the primary antibody is present at low concentrations and has substantial specificity for the antigen, the secondary binding macromolecule has substantial affinity for the Fc portion of the primary antibody, and the second binding macromolecule is affinity purified; and with (2) a detectably labeled form of the antigen; (b) incubating the mixture formed in step (a) for a time sufficient to allow the antigen and the detectably labeled antigen to competitively bind to the primary antibody of the preformed complex; (c) detecting the separated complex or the separated suspension medium.

34 Claims, 9 Drawing Figures

PRE-PRECIPITATED DOUBLE ANTIBODY IMMUNOASSAY METHOD

BACKGROUND OF THE INVENTION

This is a continuation-in-part of application Ser. No. 253,659, filed Apr. 13, 1981.

FIELD OF THE INVENTION

The present invention relates to an improvement in pre-precipitated double antibody immunoassay procedures.

DESCRIPTION OF THE PRIOR ART

The use of immunoassay methods (for example radioimmunoassay or enzyme immunoassay) for the detection and diagnosis of a wide variety of diseases and clinical conditions, has acquired great popularity in the last few years.

In a generalized competitive immunoassay method, an antibody having specificity against a predetermined antigen, is mixed with a predetermined amount of the antigen in a detectably labeled form (e.g., radio-labeled or enzyme-labeled) and with a sample of liquid containing the same antigen in unknown amounts. Incubation of this mixture is allowed to proceed so that a competition ensues between the labeled form of the antigen and the unlabeled form of the antigen for the specific binding sites of the antibody. It is necessary, after this first incubation, to separate detectably labeled antigen in its free form, from any complex of antibody with detectably labeled antigen, i.e., antigen in its bound form.

Separation of the bound from free detectably labeled antigen has been carried out in the prior art by a variety of techniques. See for example Chard, "An Introduction To Radioimmunoassay And Related Techniques", (hereinafter "Chard"), North-Holland Publishing Company, 1978, chapter 5 ("Requirements For A Binding Assay - Separation Of Bound And Free Ligand"), pages 401–425.

Precipitation of the bound complex with an antibody directed to the binder is widely used as a separation procedure in immunoassay systems. The second antibody is specific to the gamma globulin of the species in which the first antibody was raised - for example, if a guinea pig anti-insulin serum is used in the primary reaction of an assay for insulin, an anti-serum to guinea pig gamma globulins raised in a goat might be used for the separation step (Chard, pages 413–414). Separation by this technique requires a relatively large concentration of second antibody and a correspondingly large amount of the species of gamma globulins of which the first antibody forms a part must be included; for this purpose, a secondary antibody system usually involves addition of a carrier protein, either whole serum or gamma globulins, from the species in which the first antibody was raised.

The use of second antibody, however, suffers from two important practical disadvantages. The first is that it requires an additional period of incubation which may range from 15 min. to 24 hours, and can, therefore, considerably extend the time required to complete the assay. The second practical disadvantage is that of reagent supply. A new second antibody requires careful evaluation; of those which are tested, some will turn out to be completely unsatisfactory. Relatively high concentrations are required, and the product of one animal is only sufficient for a limited number of assays. Second antibody systems have therefore been considered in the prior art to be expensive.

An attempt to solve the first practical disadvantage (additional period of incubation) has been carried out by incorporating the second antibody with the primary antibody to yield a pre-precipitated complex (Chard, page 416).

The use of pre-precipitated double antibody techniques, however, has been severely criticized by the art. Chard states (p. 416) that such technique:

"permits immediate separation but may lead to loss of sensitivity and has not been widely applied".

Methods in Enzymology (Volume 70, page 270, 1980) goes even further:

This method suffers from the effects of pre-precipitation on the availability of reactive sites of the primary antibodies. Steric hindrance results in many sites becoming unavailable. Pre-precipitation thus lowers the apparent affinity and capacity of the primary antibody . . . Pre-precipitation techniques require from 5 to 10 times more antibody to bind the same amount of labeled ligand. As expected, the resulting sensitivity is also lower.

The quoted passage ends with a succint remark:
"The approach has little to commend it".

Other problems in using pre-precipitated double antibody techniques are: high mass brought about by the need of using inert immunoglobulin carrier, temperature increases needed to increase kinetics, instability, lack of consistency, difficulty in centrifuging the precipitate, as well as poor economics. Usually, in order to obtain a bell-shaped curve, high levels of primary antibody are necessary (for example, around 50–100 micrograms/ml of primary antibody). When low levels of primary antibody are used, it is usually difficult to obtain a good precipitate or a good bell-shaped curve. In any event, at low levels of primary antibody the prior art technique has been unable to provide reproducible results.

Because of the conceptual and experimental elegance of the double antibody methodology however, the art attempted to overcome the aforementioned problems by binding the secondary antibody to a solid phase. Niswender, U.S. Pat. No. 4,048,298 (1977) describes precisely such a method, wherein the second antibody is covalently bonded to a water insoluble organic polymeric substance such as cellulose or other polysaccharide, a vinyl addition polymer or condensation polymer, or a water insoluble inorganic substance of polymeric nature such as glass or silicone.

Litt, U.S. Pat. No. 4,092,408 (1978) describes the use of a polymeric substrate on which is adsorbed in solid phase an antibody composite layer comprising a precoat of the secondary antibody bound to the substrate, and a primary antibody specific to the antigen, immunologically bound to the secondary antibody. The biological fluid to be tested is contacted with the antibody surface of the composite layer to bind antigen to the primary antibody, whereupon the quantity of antigen is determined by measuring the radioactivity of the composite layer and substrate, or of the remaining biological fluid containing unbound antigen.

Tu, U.S. Pat. No. 4,166,844 (1979) describes a technique based on a test tube which has been coated on the internal surface with two antibody layers, a first layer of secondary antibodies bound chemically or physically to the internal surface of the test tube, and a second layer of specific primary antibodies which are bound chemically or physically to the secondary antibodies.

Using a different technique then preprecipitation, Ainis et al, in U.S. Pat. No. 4,189,466, disclose the use of Protein A-containing microbial cells which are sensitized with a primary antibody. Protein A is a molecule capable of binding at the Fc region of the primary antibody. The sensitized cells are mixed with antigen and agglutinate in its presence. If antigen is absent, the cells are not agglutinated. Agglutination of cells can be readily measured by nephelometric techniques. At column 4, lines 15-19, Ainis et al state that by "Protein A-containing microbial cell", they also mean to include any Protein A-containing microbial cell whether used as the intact cell, cell wall fragment, cell membrane, or any soluble substance or derivative thereof. It is difficult to see how an agglutination technique such as that of Ainis et al could be applied unless Protein A was bound to an intact cell, cell wall fragment or cell membrane. In fact, the examples in Ainis et al only disclose Protein A bound to whole cells or cell fragments.

Although the use of double antibody solid phase separations such as those of Niswender, Litt and Tu does not require the use of carrier gamma globulins, the evaluation and preparation is time consuming and the method is not widely used (Chard, p. 418).

In addition, the use of solid phase techniques brings about an increased lack of reproducibility, consistency, and accuracy due to difficulties in dispensing and titrating particulates.

A need therefore continues to exist for a pre-precipitated double antibody immunoassay method, wherein the secondary antibody is not bound to an insoluble solid phase, which does not require neutral immunoglobulin carrier, yet which maintains high accuracy, high reproducibility, high consistency, and which maximally exploits the conceptual advantages of this elegant technique.

SUMMARY OF THE INVENTION

It is therefore an object of the invention to provide a pre-precipitated double antibody immunoassay method.

Another object of the invention is to provide a pre-precipitated double antibody immunoassay method which does not require the use of an insoluble solid phase, nor the use of neutral immunoglobulin carrier.

Yet another object of the invention is to provide for a pre-precipitated double antibody immunoassay technique which has high reproducibility, high consistency, which can readily work with primary antibodies in the range of 1-40 micrograms/ml especially 1-10 micrograms/ml, wherein the antibody titer of the primary antibody is not lost, wherein nonspecific background is low, and wherein the assay is economical.

These and other objects of the invention have been attaind by providing:

An immunoassay process for the detection of an antigen in a sample, which comprises:

(a) Forming a mixture of said sample in an appropriate medium therefor with (1) a preformed complex of a primary antibody and a secondary binding macromolecule therefor, wherein said primary antibody has substantial specificity for said antigen and may be present at 1-40 μg/ml, said secondary binding macromolecule has substantial specificity for the Fc portion of said primary antibody, and said secondary binding macromolecule is affinity purified and with (2) a detectably labeled form of said antigen;

(b) Incubating the mixture formed in step (a) which comprises the complex suspended in the medium for a time sufficient to allow said antigen and said detectably labeled antigen to competitively bind to the primary antibody of said preformed complex;

c. Separating the complex from the suspension medium; and d. Detecting either the separated complex or the separated suspension medium.

Another object of the invention has been attained by providing a complex of an antibody and a binding macromolecule therefor, wherein said binding macromolecule is affinity purified and has substantial affinity for the Fc region of said antibody.

Yet another object of the invention has been attained by providing a kit comprising a carrier being compartmentalized to receive at least two containing means therein, wherein the first of said containing means comprises a preformed complex of an antibody and a binding macromolecule therefor, wherein said binding macromolecule is affinity purified and has substantial affinity for the Fc region of said antibody and said antibody may be present at 1-40 μg/ml, and the second of said containing means comprises a detectably labeled form of an antigen having reversible binding towards said primary antibody in said preformed complex.

DESCRIPTION OF THE PREFERRED EMBODIMENTS

Figure 1:
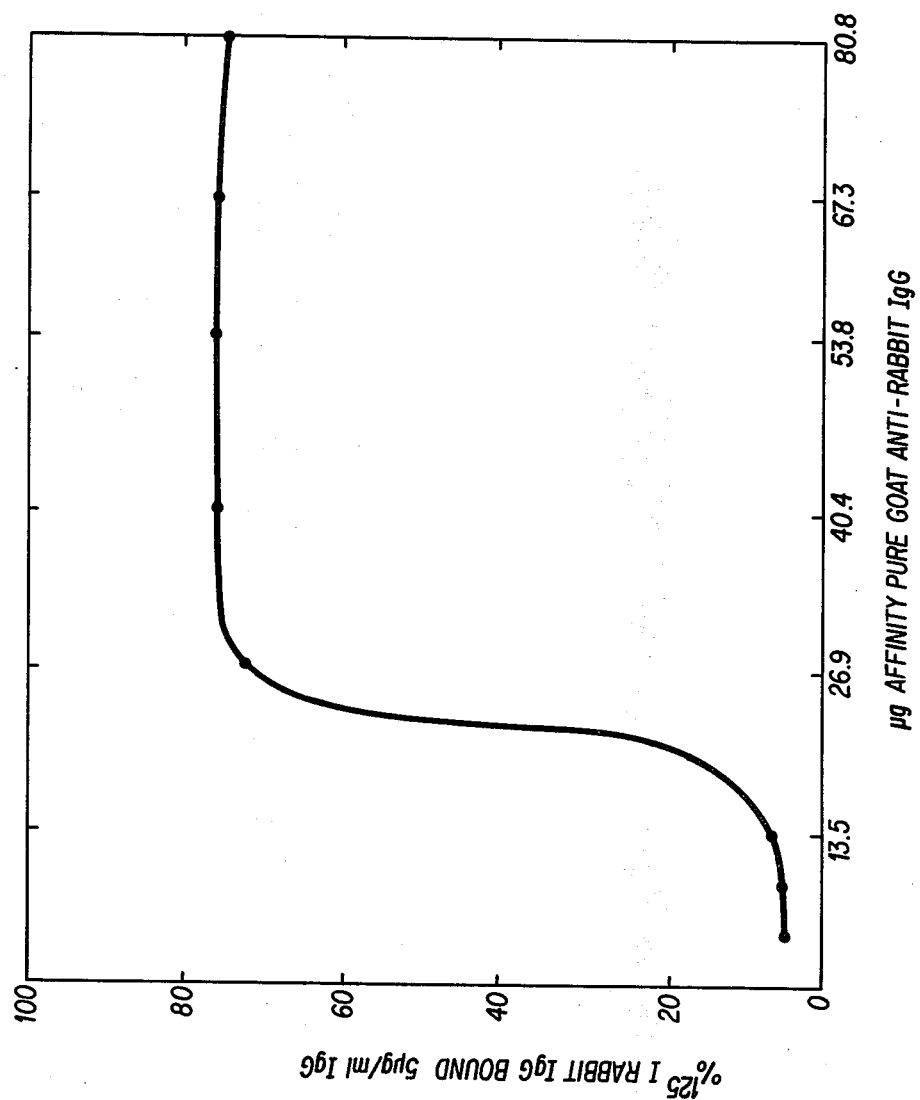

The present inventors have discovered, quite serendipitously, that the reproducibility, consistency, stability, ease of procedure, cost, as well as other characteristics described hereinafter, can be greatly improved in a pre-precipitated double antibody method, if the secondary binding macromolecule (which may or may not be an antibody) is affinity purified and has substantial specificity and affinity for the Fc region of the primary antibody. Under these conditions, it becomes possible, for the first time, to fully exploit all of the heretofore theoretical advantages of this methodology.

With this invention, it becomes possible to work at low concentrations of primary antibody, to work with little or no addition of neutral immunoglobulin carrier of the same species as the primary antibody, to work in the absence of an insoluble solid phase, and to generally obtain clean and efficient assays. Antibody titer of the primary antibody is not lost, the kinetics are essentially temperature independent, the assay variation is low, the precipitate stable and the nonspecific background (NSB) is very low. When similar assays are performed using non-affinity purified antibodies and carrier IgG, a 2-3 fold increase in NSB occurs along with a 2-3 fold decrease in primary antibody titer.

Other advantages of the methodology include (1) very small variation from tube to tube, assay to assay and day to day. Precision is increased and the possibility of technician error decreased; (2) since the volume of preprecipitated material that is being dispersed may be varied considerably (by dilution or concentration) it is easily adaptable to automated equipment for doing thousands of samples at a time if necessary, (3) approximately 30 min. to 1 hr. is saved per assay because no second antibody reaction is needed (for example, digoxin, 45 min.; $T_4$ assays, 30 min.; and $T_3$ 60 min. total); (4) there is one less pipetting step (the second antibody)

when compared to double antibody RIA. This eliminates dispensing errors in that reagent and prevents problems with second antibody optimization; (5) The preprecipitated primary antibody is homogeneous and does not require continuous mixing to stay in solution; and (6) The use of small amounts of purified reagents for the assay means lower production costs and greatly reduced shipping weight and bulk.

Generally, the process of the present invention is carried out as follows:

A sample from an animal, most usually a human, containing an antigen in unknown amounts, is incubated with a pre-formed complex of a small amount of primary antibody with substantial specificity towards said antigen and a secondary binding macromolecule, having substantial binding affinity for the Fc region of said primary antibody and being affinity purified. This mixture is incubated with a known amount of detectably labeled antigen. The mixture is allowed to incubate so that labeled antigen and unlabeled antigen can compete for the binding sites of the primary antibody in the complex. After an appropriate time for incubation, the complex is separated from the medium in which it is suspended. The separation can be normally carried out by centrifugation and decantation or aspiration of the supernatant solution. Thereafter, the amount of label bound to the complex, or the amount of label remaining in the supernatant is detected. In this manner, a ratio of bound to free label can be obtained, and interpolated into a standard curve prepared beforehand for the system. The methodology of immunoassay incubation, separation and interpolation into a standard curve is well known, and reference is made to Chard, herein incorporated by reference, especially chapters 5, 6 and 7.

The specific improvement brought about by this invention relates to the use, as the secondary binding macromolecule, of an affinity purified binding macromolecule having substantial affinity and specificity for the Fc region of the primary antibody. This combination of factors is responsible for the suprisingly effective results observed in the invention.

These factors are also responsible for the ability to precipitate very low levels of primary antibody, i.e., 1–40 $\mu$g/ml, preferably 1–10 $\mu$g/ml. At levels higher than about 40 $\mu$g/ml, the assays become difficult, the reaction slows down, clumps arise, NSB rises and the pellets become unstable.

The secondary binding macromolecule may or may not be an antibody. Non-antibody binding macromolecules may include molecules which specifically bind the Fc region of immunoglobulins and capable of forming a three-dimensional network and insoluble precipitate with primary antibody. When it is an antibody, it is prepared by raising the same in an appropriate animal, by injection into said animal of antibody-producing amounts of the Fc fragment of the primary antibody, or intact primary IgG, wherein said primary antibody is normally from a different species. Alternatively, the secondary antibody may be a monoclonal antibody obtained from a hybridoma or from the ascites fluid of an appropriate animal (see e.g., Scientific American, 243:66 (1980) herein incorporated by reference).

The preparation and isolation of Fc fragments from immunoglobulins, or of immunologically functional products of immunoglobulins which contain the Fc portion are known processes, described, e.g., in Franek, Biochem. Biophys. Res. Comm, 4:28 (1961). Fc fragments, or subfragments thereof obtained from immunoglobulins after enzymatic treatment for example with papain, plasmin or pepsin are described, for example, in: Bennich, H. and Turner, M. W., Biochem. Biophys. Acta. 175:388 (1969); Reid, K. B. M. Immunology 20:649 (1971); Porter, R. R., The Biochemical Journal 73:119 (1959); Haupt, H. and Heide, K. Klin. Wschr. 47:270 (1969); Hershgold, E. J. et al Nature, 199:284 (1963), herein incorporated by reference.

After sensitization and antibody formation in the second animal, the animal is bled and the secondary antibody, having substantial affinity for the Fc fragment is purified therefrom. Purification of the antibody needs to be carried out by affinity chromatography; a prepurification, such as for example by ammonium sulfate precipitation may facilitate the procedure.

Affinity chromatography or immunoabsorbent chromatography of antibodies is a well known technique. In the present invention, an insoluble solid phase is prepared, and the Fc framgent or an immunologically functional product of immunoglobulin with immunologically functioning Fc is bound to the solid phase, preferably by covalent immobilization. The attachment of proteinaceous materials to resins is a well known technique in the art and will not be discussed further. The impure or partially purified secondary antibody is brought into contact with the solid phase-bound Fc fragment, and binds thereto. When immunization has been carried out with Fc fragments the affinity column may contain intact IgG bound thereto. Antibodies and other materials which do not have specificity for the Fc fragment do not bind to the solid phase and remain in solution. The solid phase carrier or resin can be contacted with the solution containing the mixture of antibodies either in batch or in a column process. After separation of the original solution and washing of the carrier, the adsorbed secondary antibody is separated from the carrier by a solution containing a desorption agent such as an acid, a base or a high salt solution. After collecting fractions which contain the secondary antibody, the same can be freed of salts, acids or bases by dialysis, diafiltration or similar methodology.

Because human IgG present in a sample may, (when a secondary macromolecule has substantial cross reactivity with human IgG) may dissociate or tend to dissociate preformed complexes, it may be desired to remove from the affinity purified secondary binding macromolecule, any cross-reactivity with human IgG. In such instances, the affinity purified secondary macromolecule is further contacted (in batch or column) with solid phase-bound human IgG. The bound material is discarded, while the non-bound material is collected and used.

Alternatively, the secondary antibody can be raised in an animal by injecting into the animal whole primary antibody. This produces in the animal a family of secondary antibodies most of which have specificity for the Fc region of the primary antibody, and some of which have specificity for the binding regions (F(ab)) of the primary antibody. After prepurification by ammonium sulfate precipitation if necessary, this mixture of antibodies is purified by immunoaffinity chromatography as previously described, against a solid phase containing covalently bound Fc fragments or immunologically functional products of immunoglobulins containing functional Fc fragments.

The primary antibody may include the well known immunoglobulins, comprising IgG, IgM, IgA, IgD, and IgE although only IgG is usually of concern. It may be obtained by direct immunization schedules with the immunogen or from hybridomas or ascites fluid of appropriate animals (Scientific American, 243:60 (1980)). Immunization schedules are well known in the art (Chard, pages. 386-387). Immunogens for which a test is desired can be injected with adjuvant into antibody-producing animals such as horses, goats, rabbits, guinea pigs, an the like. Materials of low molecular weight (e.g., steroid hormones) are generally non-immunogenic, but become so when conjugated as "haptens" to larger molecules such as albumin. Factors which may enhance the response to a conjugate include a high density of hapten on the carrier, or the use of a carrier which is itself immunogenic.

In the vast majority of immunization schedules the antigen is injected as an emulsion in "complete Freund's adjuvant". This is a mixture of mineral oil, detergent and killed mycobacteria.

An immunization program, as is well known in the art, will yield a number of anti-sera from which one or more must be selected for use in an assay. The criteria for this selection are generally specificity, affinity and titer, (Chard, pages 393-396). The antibodies having the desired specificity and affinity can be prepurified by ammonium sulfate precipitation. In some cases affinity chromatography on a column or batch containing the immunogen or antigen covalently bound to a solid phase is used to further purify the antibody.

The complex of secondary binding macromolecule and primary antibody is formed before the preparation of the assay. A solution of secondary binding macromolecule is very slowly added to primary antibody in an appropriate physiological buffer (Tris, Hepes, Pipes, imidazole, glycerol phosphate, etc.). The rate of addition has to be sufficiently slow to prevent flocculation of the complexes. For example, addition at a rate of about 1-2 minutes/mg of primary antibody precipitated is sufficient. After completing addition, the suspension is incubated at 4° C.-30° C., preferably room temperature, for a period sufficient to cause substantially complete formation of the complex and precipitation thereof. A period of 1-4 hours is generally sufficient. The material is then incubated at 4° C. for about 24 hours. The ratio of secondary binding macromolecule to primary antibody is normally that which is sufficient to completely precipitate the primary antibody, such as 4.5-50:1, normally 10-15:1.

Once formation and precipitation of the complex has occurred, the same remains suspended in the original buffer. The complex is stored at 4° C. Although preliminary experiments with freezing or lyophilization indicate that the complex loses titer and forms clumps, it is expected that further investigations will elucidate conditions under which the complex can be stored frozen or lyophilized. These states of the complex are therefore envisioned in the present invention.

Neither the primary antibody nor the secondary binding macromolecule in the preformed complex of the present invention are bound covalently or noncovalently, physically or chemically to a solid phase which is insoluble in aqueous buffers. This characteristic of the invention distinguishes the same from the solid phase-containing double antibody methods of Niswender, Tu and Litt mentioned previously. Thus, the components of the preformed complex are free from such materials as water insoluble organic polymeric substances including cellulose or other polysaccharides; vinyl addition polymers or condensation polymers such as aminoplasts or polyesters; water insoluble inorganic substances of polymeric nature such as glass or silicone resins; or solid supports such as polystyrene or polypropylene.

The complex and the secondary binding macromolecule are also free from intact microbial cells, cell wall fragments, cell membranes or derivatives thereof.

Furthermore, the complexes of secondary binding macromolecule and primary antibody in the present invention usually do not need nor contain neutral inert immunoglobulin G carrier of the same species as the primary antibody, a material normally required by the pre-precipitated double antibody techniques of the prior art. It is possible in using the complex of the present invention to dispense with this material. However, it may be desired under certain conditions where very high titered primary antibody is used and the IgG mass falls below 1-10 $\mu$g/ml.

In using the technique of the present invention, the word "antigen" is meant to include any measurable substance including high molecular weight or low molecular weight substances present in a sample of an animal, including humans. The samples may be liquid (such as for example urine, saliva, blood, serum, and the like) or solid or semi-solid (tissues, feces, and the like).

Measurable substances include for instance human chorionic gonadotropin, growth hormone, insulin, glucagon, adrenocorticotropic hormone, thyroid stimulating hormone, immunoglobulin E, a-fetoprotein, hepatitis B antigen, human placental lactogen and their antibody; steroids such as testosterone, estriol, cortisol, progesterone, corticosterone, aldosterone; thyroid hormones such as thyroxine, triiodothyronine; thyroid binding globulin (TBG); active peptides such as bradykinin, gastrin, angiotensin, thyroid hormone-releasing hormone, luteinizing hormone-releasing hormone; physiologically active amines such as epinephrine, norepinephrine, histamine, serotonin; prostaglandins, such as $PGF_{2a}$, PGE, thromboxanes, prostacyclins, etc.

The antigen is labeled with a detectable label such as a radiolabel, a fluorescent label, an enzyme label, a free radical label or a bacteriophage label (see Chard, Chapter 3, pages 343-376). Most commonly, the label is a radiolabel (radioimmunoassay) or an enzyme label (enzyme immunoassay). The more common radiolabels are $^{125}I$, $^{131}I$, $^{3}H$, $^{14}C$. Among the common enzyme labels are horseradish peroxidase, alkaline phosphatase, $\beta$-D-galactosidase, glucose oxidase, glucoamylase. Among the fluorescent materials are, for example, fluorescein isothiocyanate, and rhodamine.

In carrying out the immunoassay according to the process of the invention, an animal sample containing the measurable antigen is mixed with an appropriate buffer containing a known amount of detectably labeled antigen and with the preformed complex. After a period of incubation sufficiently long to permit complete competitive equilibration between labeled and unlabeled antigen at the binding site of the primary antibody in said complex, separation by centrifugation is carried out, and either the complex or the separated supernatant solution are detected, as by counting, addition of an enzyme substrate, or fluorescence measurement, and the like. The period of incubation depends upon the affinity and dose-response characteristics of the primary antibody and can be readily determined by the user by conventional titration techniques. The method of this invention does not affect these two characteristics of the primary antibody. For example, periods can range from 30 minutes to 24 hours, preferably 30 minutes to 2 hours.

The quantitative result is interpolated into a standard curve as described previously, (See also Chard, chapter 7, pages 440-445).

The materials for use in the assay of the invention are ideally suited for the preparation of a kit. Such a kit may comprise a carrier means being compartmentalized to receive in close confinement one or more container means such as vials, test tubes, and the like, each of said container means comprising one of the separate elements to be used in the method. For example one of said container means may comprise a preformed complex of secondary binding macromolecule and primary antibody, wherein the primary antibody has specificity against a given antigen. This complex may be in solution of an appropriate physiologically compatible buffer or may eventually be in lyophilized form. Said first container means may also include a predetermined, known amount of the detectably labeled given antigen. Alternatively, and preferably, a predetermined known amount of the detectably labeled antigen may be present in a second container means in the compartmentalized carrier, either in an appropriate physiologically acceptable solution or in lyophilized form. The carrier may also contain in addition, a plurality of container means each of which comprises a mixture of detectably labeled antigen and non-labeled form of the same antigen, each of said mixtures having a different molar ratio of detectably labeled to non-labeled antigen.

If the first container means comprises both the preformed complex and the known amount of detectably labeled antigen, all the user has to do is add a premeasured amount of animal sample containing the mesurable yet unknown amount of antigen in a buffer to said first container means, or the whole into a separate container means. Incubation is then allowed to proceed as described previously and thereafter, complex is separated by centrifugation or other separation technique, and the label is detected either on the separated complex or on the separated supernatant. In this mode, incubation times are somewhat longer because of the need to displace the labeled antigen by reverse equilibration.

If the first container means comprises preformed complex and the second container means comprises the known amount of labeled antigen in buffer, all the user has to do is add a premeasured amount of measurable yet unknown antigen in the animal sample in a small amount of buffer to the second container means, or the whole into a separate container means, mix for a few seconds and then add this mixture to the first container means. Incubation and separation as well as detection are then allowed to proceed as previously.

The plurality of container means comprising predetermined known, different ratios of labeled to unlabeled antigen are used in order to prepare a standard curve for the given antigen, utilized in the interpolation and analysis of the results.

A different kit can be prepared for each antigen, or a given kit may contain sufficient materials for the detection of a family of antigens, such as for example the thyroid hormones.

Having now generally described this invention, the same will become better understood by reference to certain specific examples which are included herein for purposes of illustration only and are not intended to be limiting thereof unless specified.

EXAMPLE 1

A goat-rabbit IgG (GARGG) antibody obtained by immunization with rabbit IgG and containing mostly anti-Fc was purified by passage through a column of Sepharose-4B containing rabbit IgG Fc fragments immobilized thereon. Affinity purified GARGG was separated from the column by 0.58% acetic acid elution and titrated against 5 $\mu$g/ml of $^{125}$I-rabbit IgG. The results are shown in FIG. 1. A broad region of binding capacity is obtained.

Figure 2:
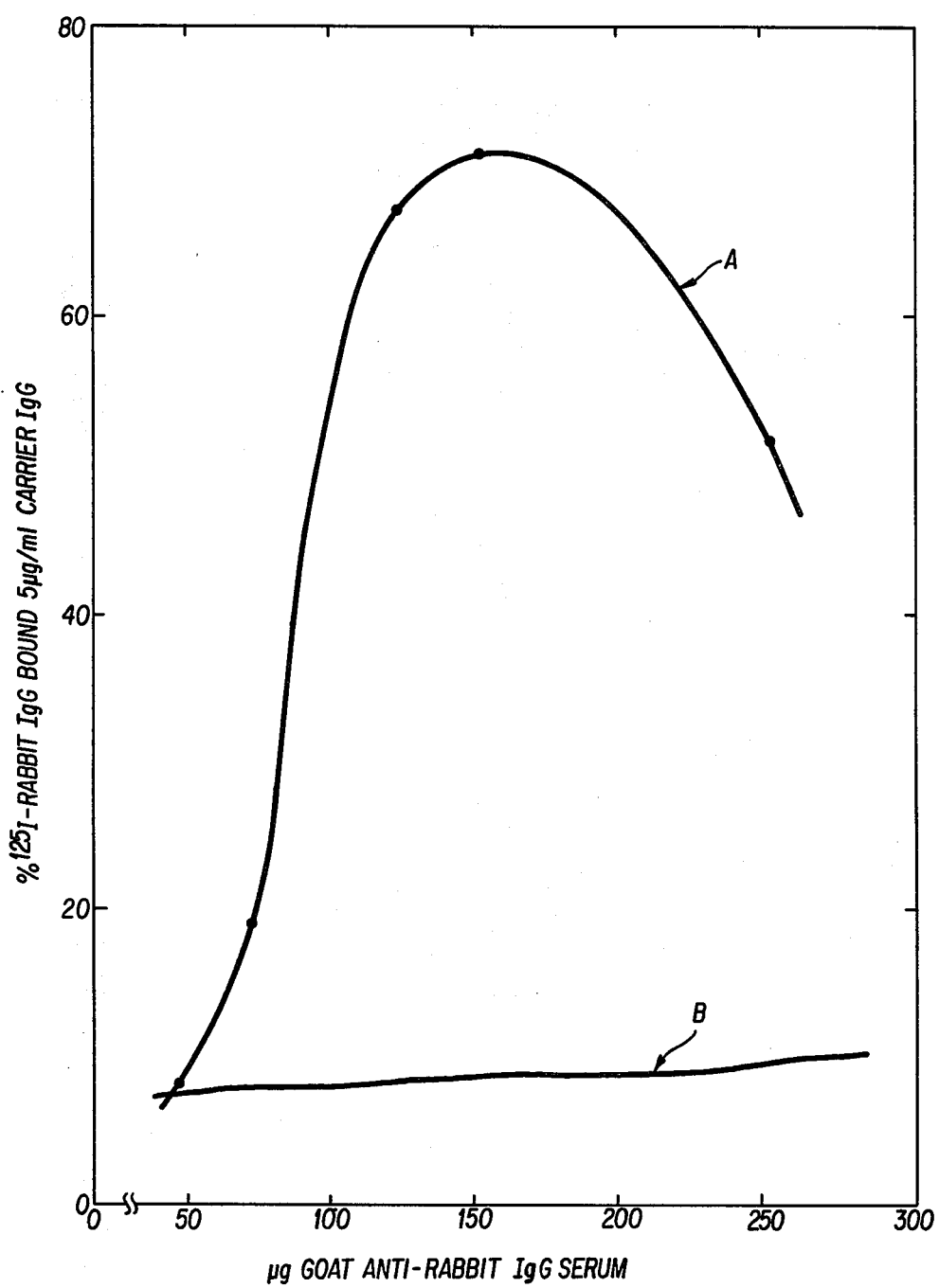

An analogous experiment wherein GARGG was not affinity purified is shown in FIG. 2. Curve A represents the titration curve obtained for 5 $\mu$g/ml of rabbit IgG with an exceptionally good GARGG. Curve B is a representation of the more common non-bell shaped curve obtained at such low levels of primary antibody.

EXAMPLE 2

Figure 3:
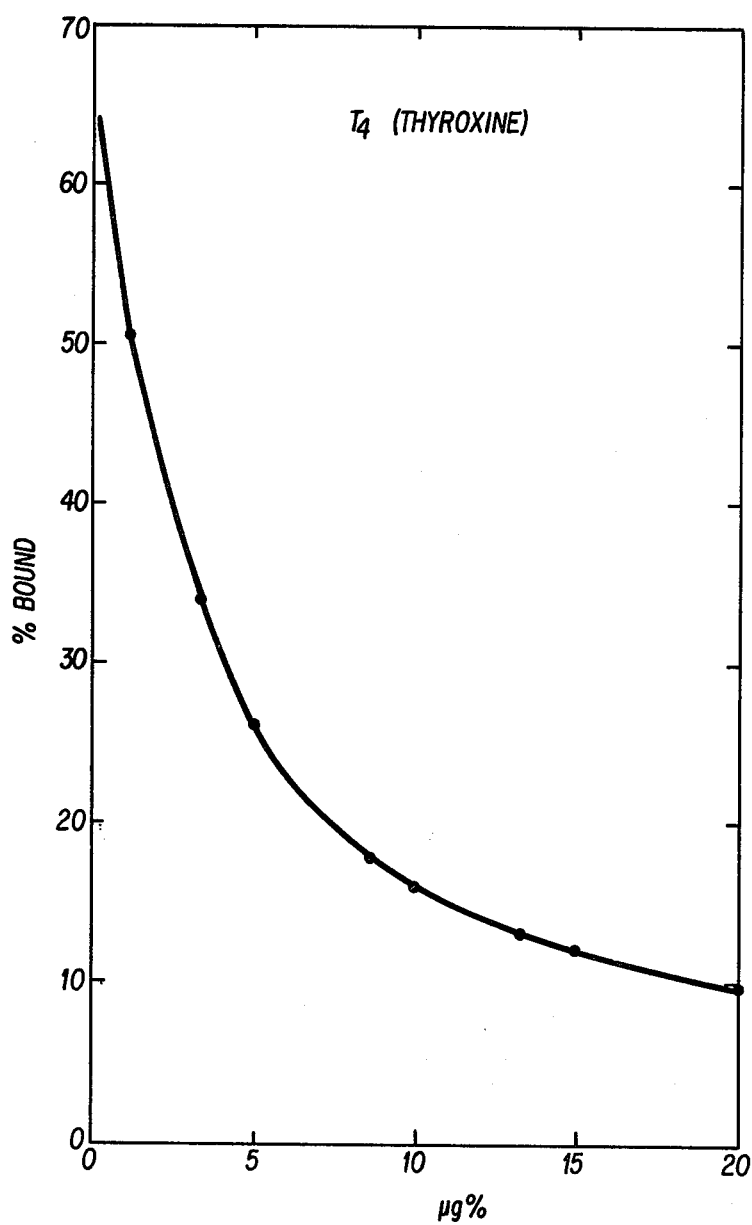

Affinity purified GARGG was prepared as in Example 1, and a compelx was prepared thereof with anti-$T_4$ rabbit IgG. Incubation time: 24 hrs; ratio of GARGG to rabbit IgG: 15:1; concentration of rabbit IgG: 10 $\mu$g/ml. The complex was then used at 1.5 $\mu$g/per tube in a radioimmunoassay in the determination of human $T_4$ and the results are shown in FIG. 3.

EXAMPLE 3

Figure 4:
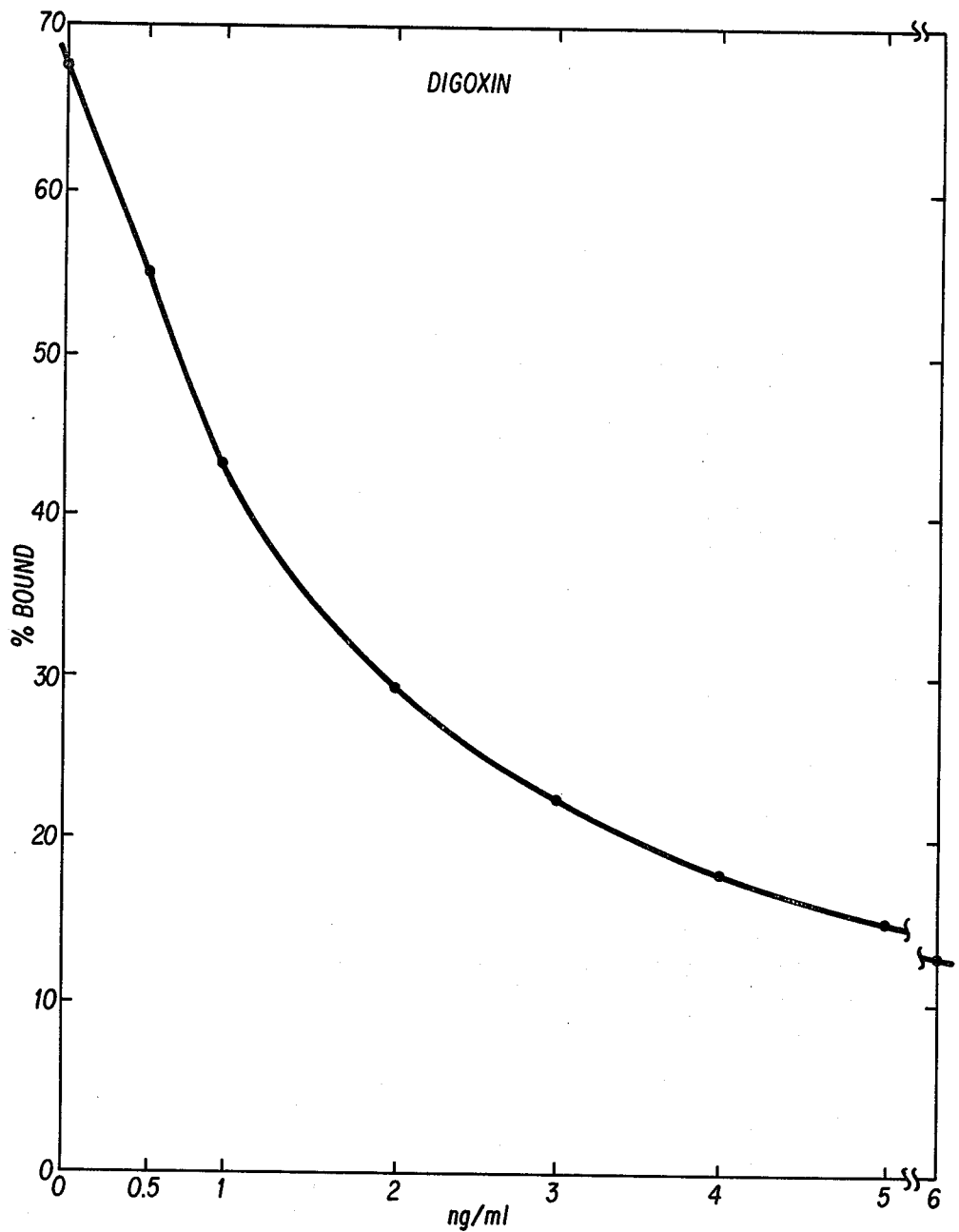

The determination of human digoxin from serum using the GARGG of Example 2 and anti-digoxin rabbit IgG in a preformed complex is shown in FIG. 4.

EXAMPLE 5

Figure 5:
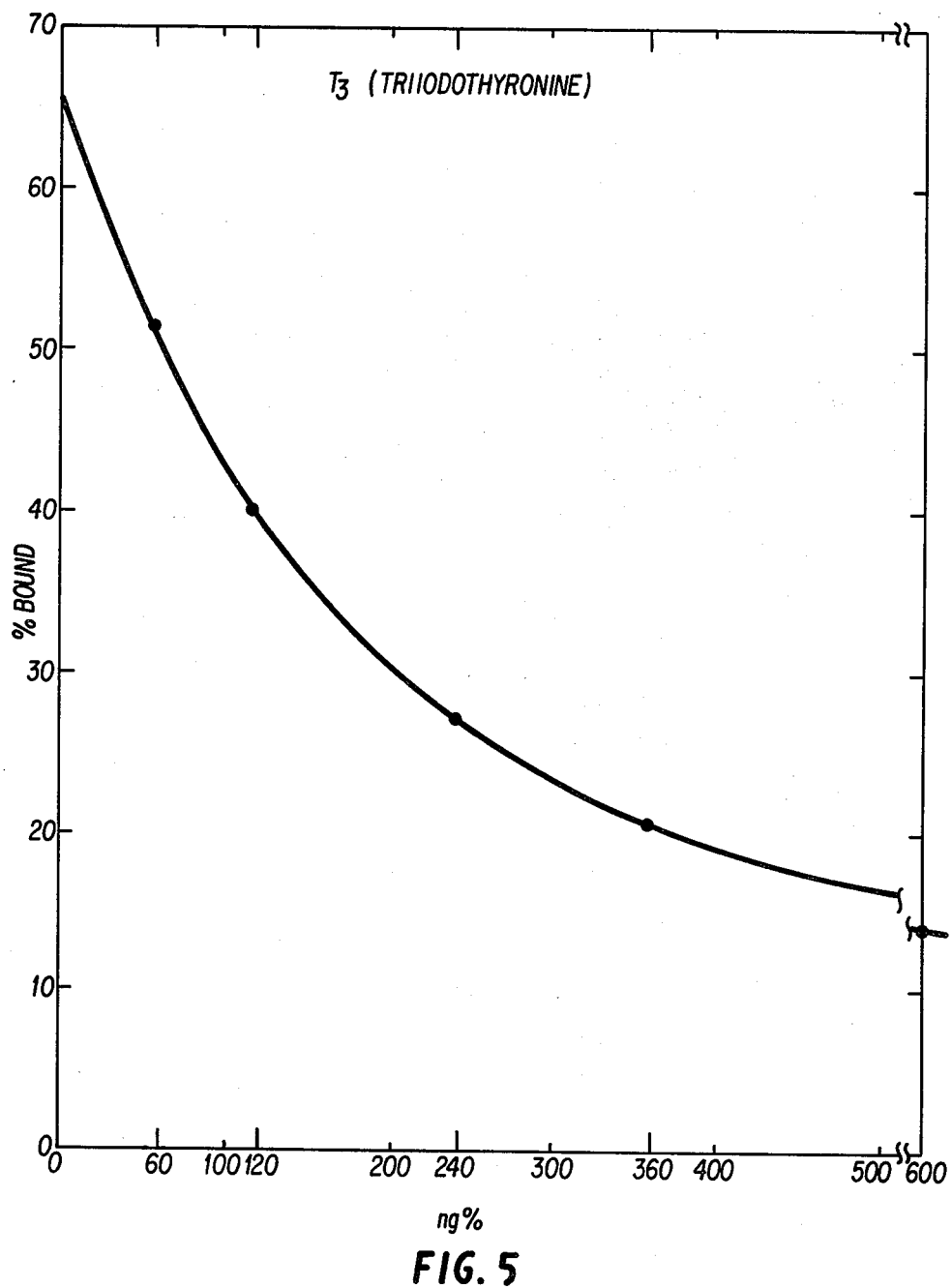

The determination of human $T_3$ from serum using the GARGG of Example 2, an anti-$T_3$ rabbit IgG in a preformed complex is shown in FIG. 5.

COMPARATIVE EXAMPLE 5

The determination of human $T_3$ from serum using non-affinity purified GARGG, and anti-$T_3$ rabbit IgG in a performed complex, wherein the anti-$T_3$ IgG is present at 10 $\mu$g/ml gave poor results. The pre-precipitate was difficult to disperse as it flocculated into granules. Titration indicated that titer had decreased 3-fold.

EXAMPLE 6

Figure 6:
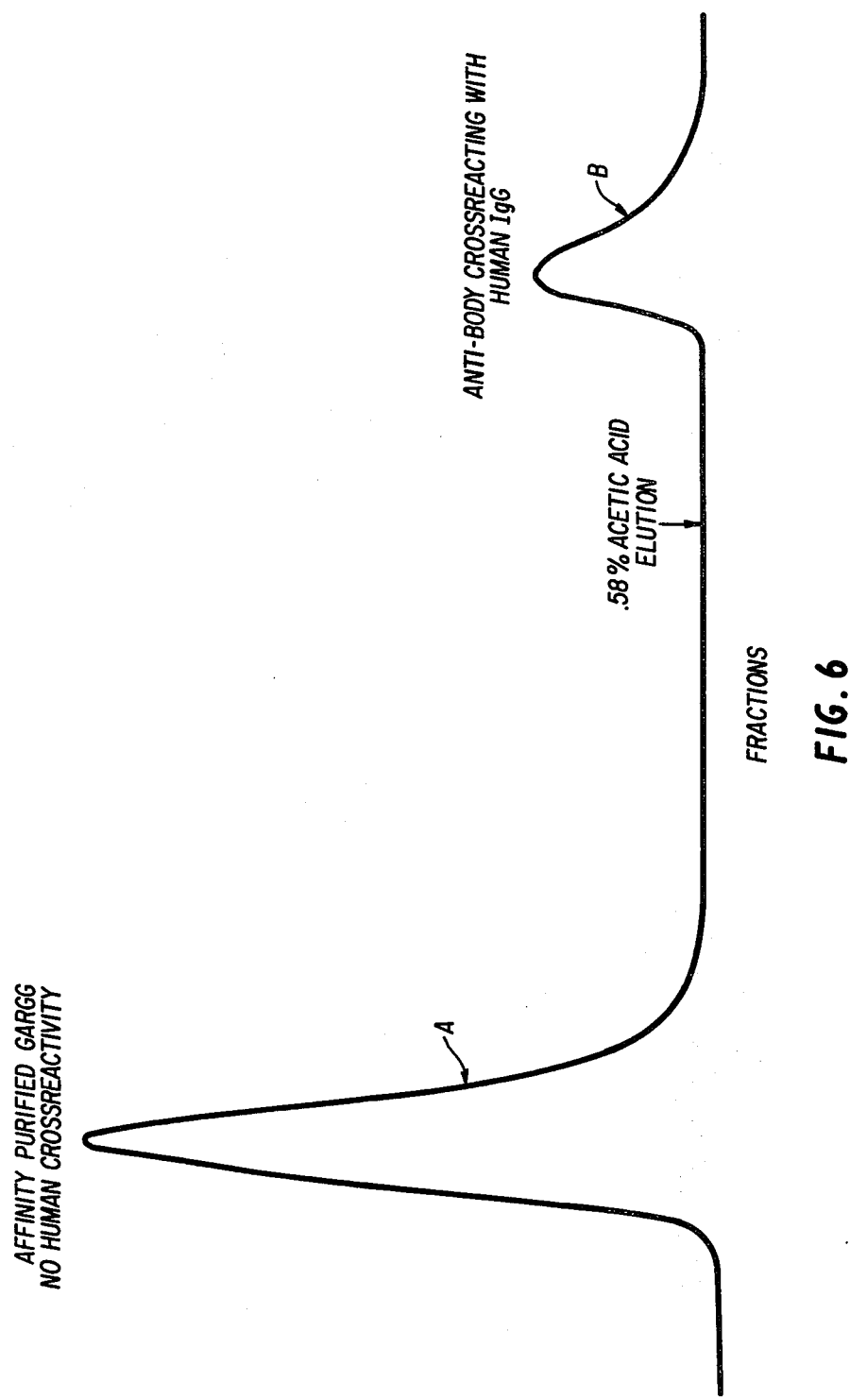

Goat anti rabbit IgG mostly specific for the Fc region obtained by immunization with rabbit IgG was first affinity purified on a column of Sepharose 4-B having rabbit IgG Fc fragments bound thereon, as described in Example 1. The material was then further affinity purified by passage through a column containing human IgG bound thereon. The results of the second chromatography are shown in FIG. 6. Peak A represents nonbound GARGG having essentially no crossreactivity with human IgG; it elutes in the void volume. Peak B is eluted after changing the elution medium to 0.58% acetic acid, and contains GARGG having cross-reactivity with human IgG.

Figure 7:
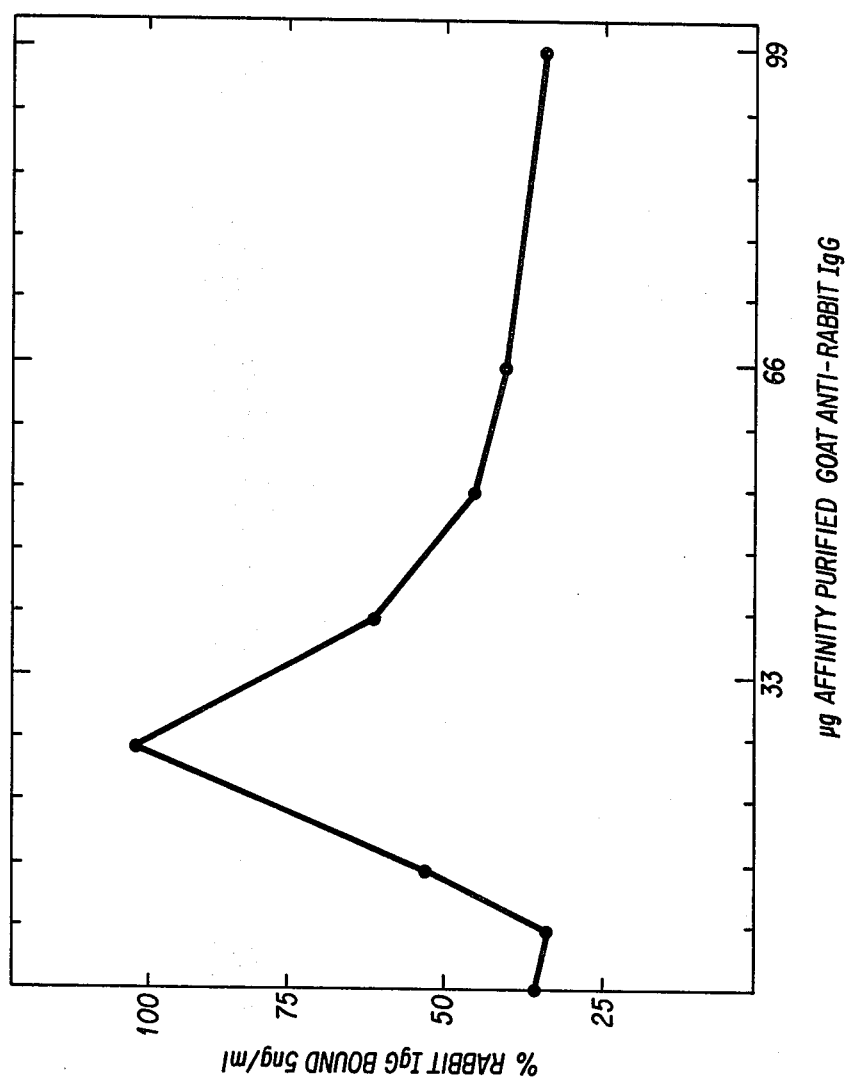

The non cross-reactive material from peak A was titrated with $^{125}$I-rabbit IgG in the 5$\mu$g/ml range and the results are shown in FIG. 7. A much sharper optimum is seen.

Figure 8:
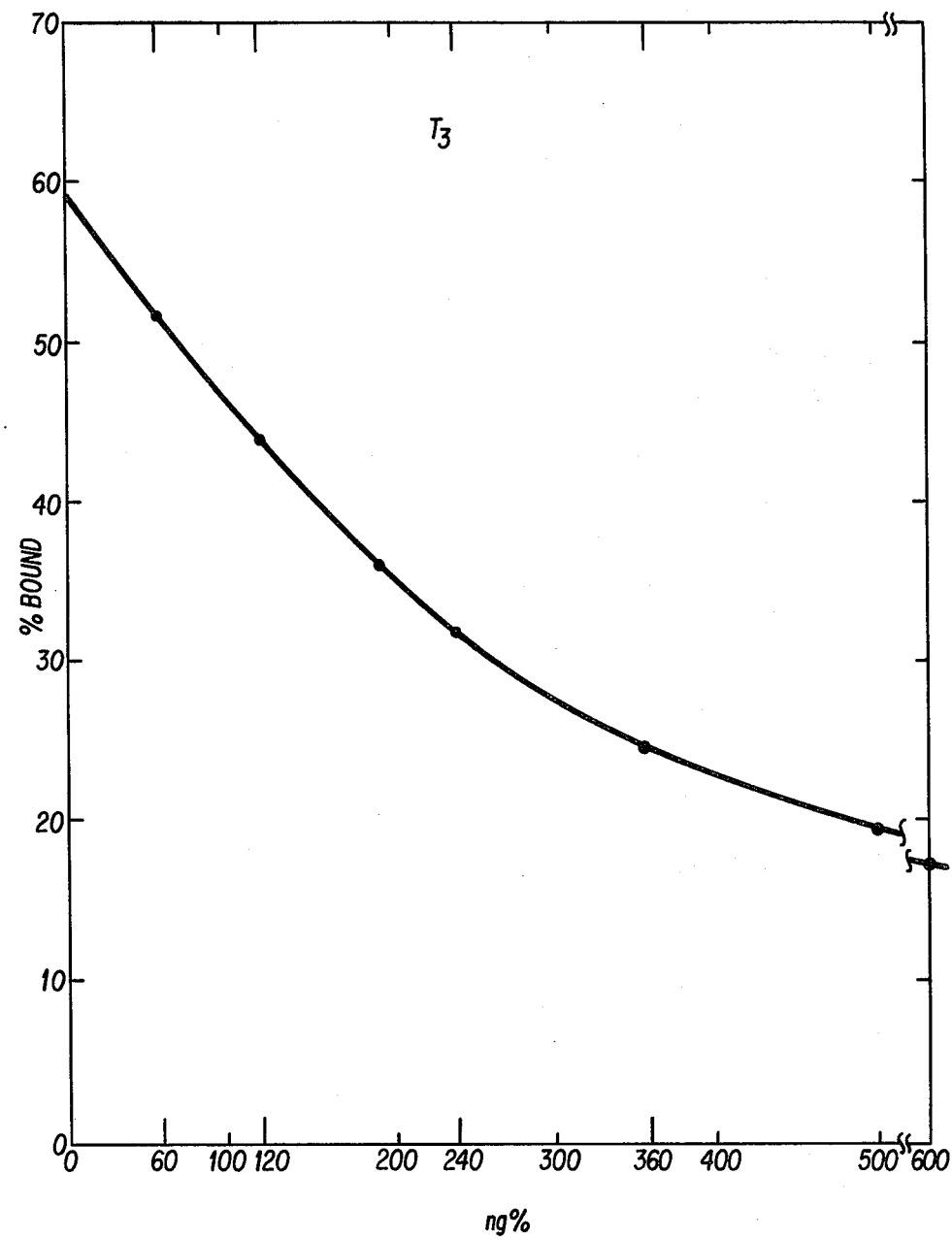

The material from peak A was used to form a pre-precipitated complex with anti-$T_3$ rabbit IgG, and used in a radiommunoassay for $T_3$. The results are shown in FIG. 8. In some cases where the assay time is long and sample volume large, cross reactivity between rabbit and human IgG may cause dissociation of pre-precipitated immune complexes. Affinity absorbtion of cross reacting antibody can prevent this.

EXAMPLE 7

Figure 9:
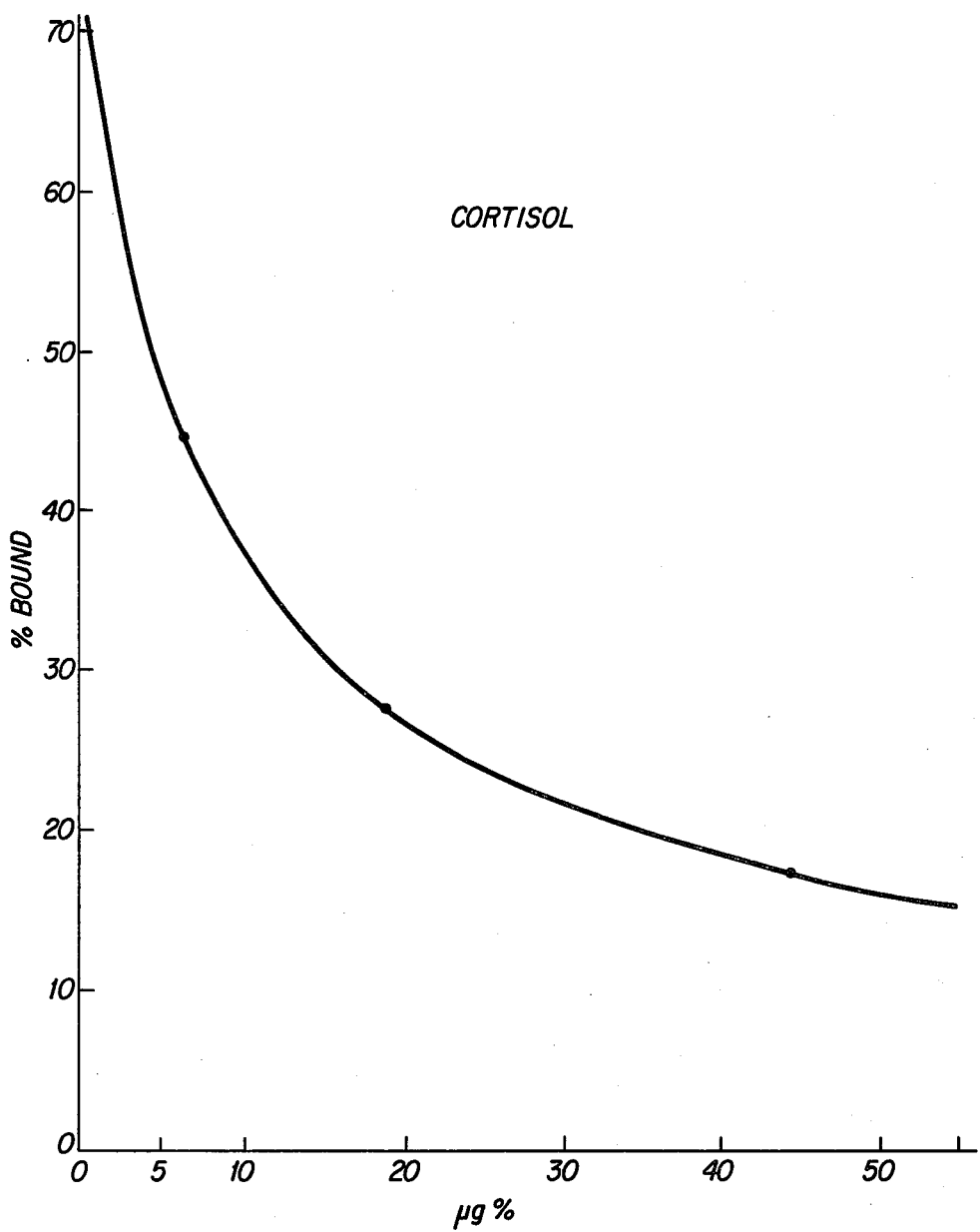

The determination of human cortisol from serum using the GARGG of Example 2 and anti-cortisol rabbit IgG in a preformed complex is shown in FIG. 9.

EXAMPLE 8

Measurement of the Unsaturated Capacity of thyroxine Binding Globulin (TBG) in serum to bind $T_3$.

$T_3$ and $T_4$ circulate in the bloodstream principally bound to plasma proteins, such as TBG. A very small proportion of each hormone exists in the free state and is the physiologically active hormone, while the TBG-bound hormone is not active. A change in the ability of a patient's serum TBG to bind $T_3$ will result in a proportionate change in the amount of free $T_3$. The present protocol is based on the comparison of the TBG binding capacity of a patient's sample to that of a known serum standard. Standard serum (Human serum with 0.1% sodium azide) and patient sample are added to separate tubes, followed by measured amounts of $^{125}I\text{-}T_3$ (0.1% gelatin, 0.1M Phosphate Buffered Saline 0.15% Sodium Azide, 0.2 mM EDTA, Human Serum). Next a preformed complex such as that of Example 5 is added to both patient and standard tubes, and incubated at room temperature for 5 minutes. During incubation, the unsaturated TBG in the patient serum samples bind the $^{125}I\text{-}T_3$ to the limits of their respective capacities. The $^{125}I\text{-}T_3$ not taken up by the serum TBG is absorbed by the sorbent. Tubes are then centrifuged, the supernatant discarded and the radioactivity of the pelleted sorbent is measured in a gamma counter.

EXAMPLE 9

A kit was prepared for the quantitative measurements of total thyroxine levels in serum plasma. The kit contained a first container with 0.05% tris maleate, 0.2 mM EDTA, ANS, salicyclic acid, 0.1% sodium azide and a yellow dye. The buffer contained less than 10 microcuries of $^{125}I\text{-}T_4$. A second container contained insolubilized complex antiserum with 0.1% gelatin, 0.1% sodium azide and 0.02 M phosphate buffer, insolublized $T_4$ antiserum, and blue dye. Insoluble antibody is titrated to bind about 50% of the labeled thyroxine in the absence of unlabeled thyroxine. A third container contained red insolubilized neutral rabbit IgG with 0.1% gelatin, 0.1% sodium azide and 0.02 M phosphate buffer, insolubilized neutral rabbit IgG and red dye. Total protein concentration is adjusted to a concentration equivalent to that of the insolubilized $T_4$ antibody reagent. A series of six containers were present in the kit containing $T_4$ standards wih L-thyroxine based on human serum with 0.1% sodium azide at concentrations 0, 1, 5, 10, 15, 20 micro grams/dL. In order to carry out a $T_4$ assay procedure with this kit the following steps are used. All reagents are brought to room temperature and mixed well. 500 microliters of $^{125}I\text{-}T_4$ buffer are added to each tube. To each tube are than additionally added 10 microliters of standards, serum samples and controls. 10 microliters of zero standard (STD A) are added to each tube. The insolubilized $T_4$ antibody is mixed by inversion to disperse any material that may have settled in the bottle. Within 15 minutes after mixing 500 microliters of this, antibody is added to all tubes except total activity and non specific binding (NSN) tubes. Tubes are vortexed or shaken gently and, by mixture of colors turn green. The red insolubilized neutral rabbit IgG is mixed well by inversion to disperse any material that may have been settled. Within 15 minutes after mixing, 500 microliters of this IgG is added to NSB tubes. The tubes are vortexed or shaken gently, and the tubes will then be orange. All tubes are incubated for a minimum of 30 minutes at room temperature. All tubes are centrifuged except total activity tubes, at 2,000 xg for 10 minutes, preferably at 4° C. Within 10 minutes after centrifugation, all tubes are decanted or aspirated, except total activity tubes. Tubes are inverted simultaneously and allowed to drain 30 to 60 seconds on a blotter. All tubes are then placed in a gamma counter and radioactive counting is carried out.

EXAMPLE 10

A digoxin kit was prepared with the following containers. The first container contained $^{125}I$-digoxin buffer containing 0.02 mol/L phosphate buffer saline, 0.1% gelatin, 0.1% sodium azide and a yellow dye, the buffer containing less than 10 microcuries. A second container contained insolubilized digoxin antibody with 0.1% gelatin, 0.1% sodium azide and 0.02 mol/L phosphate buffer, insolubilized digoxin antiserum (rabbit) and a blue dye. The insolubilized antibody is titrated to bind about 50% of the labeled digoxin in the absence of unlabeled digoxin (the zero standard tube).

A third container contained insolubilized neutral rabbit IgG with 0.1% gelatin, 0.1% sodium azide and 0.02 mol/L phosphate, insolubilized neutral rabbit IgG and a red day. Total protein concentration is adjusted to a concentration equivalent to that of insolubilized digoxin antibody reagent. Finally, the kit contained digoxin standards based on human serum with 0.1% sodium azide in concentrations nominally 0, 0.5, 0.1, 2.0, 3.0, 4.0, 6.0 and ng/ml.

For the determination of digoxin, the following procedure can be carried out with this kit. All reagents are brought to room temperature and mixed well. Five hundred microliters of yellow $^{125}I$-digoxin buffer are added to each tube. Fifty microliters of standards, serum samples and controls are added to appropriately labeled tubes. Fifty microliters of zero standard (STD A) is added to each Non Specific Binding (NSB) tube. The blue insolubilized digoxin antibody is mixed well by inversion to disperse any material that may have settled in the bottle. Within 15 minutes after mixing, 500 microliters of this antibody are added to all tubes, except total activity and NSB. Tubes are vortexed or shaken gently. The tubes will then be green. The red insolubilized neutral IgG is mixed well by inversion to disperse any material that may have settled in the bottle. Within 15 minutes after mixing, 500 microliters of this IgG is added to NSB tubes. The tubes are vortexed or shaken gently and the tubes will then be orange. In standard procedure all tubes are incubated for a minimum of 45 minutes at room temperature. In STAT procedure tubes are incubated for 20 minutes at 37° C. Finally, tubes are centrifuged, except total activity tubes, at 2000 xg for 10 minutes preferably at 4° C. Within 10 minutes after centrifugation all tubes except total activity tubes are decanted or aspirated. Tubes are inverted simultaneously and allowed to drain 30 to 60 seconds on a blotter. Finally, tubes except total activity and NSB tubes, are placed in a gamma counter for radioactive counting.

EXAMPLE 11

A kit for the quantitative measurement of total triiodo thyronine levels in serum or plasma was prepared containing the following: A first container with $^{125}$I-T$_3$ buffer with 0.1 M phosphate buffer, 0.2 mM EDTA, NAS, Thimerosal, 0.1% sodium azide and a yellow dye; the buffer containing less than 10 microcuries. A second container contained insolubilized antiserum with 0.1% gelatin, 0.1% sodium azide and 0.02 M phosphate buffer, insolubilized T$_3$ rabbit antiserum and a blue dye. The primary antibody is generated by immunizing rabbits with T$_3$, purified from antiserum and insolubilized. Insoluble antibody is titrated to bind about 50% of the labeled T$_3$ in the absence of unlabeled T$_3$. A third container contained insolubilized neutral rabbit IgG with 0.1% gelatin, 0.1% sodium azide and 0.02% M phosphate buffer, insolubilized neutral rabbit IgG and a red dye. Total protein concentration is adjusted to a concentration equivalent to that of the insolubilized T$_3$ antibody reagent. A set of T$_3$ standards contain triiodothyronine based on human serum with 0.1% sodium azide at concentrations nominally 0, 50, 150, 300, 450, 600 ng/dL.

In the measurement of T$_3$ the following procedure is utilized. All reagents are brought to room temperature and mixed well. 500 microliters of the yellow $^{125}$I-T$_3$ buffer are added to each tube. 200 microliter standards, serum sample and controls are added to appropriately labeled tubes. 200 microliters of zero standards (SDT A) are added to each nonspecific binding (NSB) tube. The blue insolubilized T$_3$ antibody is mixed well by inversion to disperse any material that may have settled in the bottle. Within 15 minutes after mixing, 500 microliters of this antibody is added to all tubes except total activity and NSB tubes. The tubes are shaken gently. The tubes will then be green. The red insolubilized neutral rabbit IgG is mixed well by inversion to disperse any material that may have settled within the bottle. Within 15 minutes after mixing, 500 microliters of this IgG is added to NSB tubes. The tubes are shaken gently and they will then be orange. All tubes are incubated for a minimum of 60 minutes at room temperature. All tubes except total activity tubes are centrifuged, at 2,000 xg, at 10 minutes preferably at 4° C. Within 10 minutes, after centrifugation the tubes except total activity tubes are decanted or aspirated. The tubes are simultaneously inverted and allowed to drain 30 to 60 seconds on a blotter. All tubes including total activity and NSB tubes are placed in the gamma counter for radioactive counting.

Having fully described this invention it will be readily ascertained by those skilled in the art that the same can be carried out within an equivalent range of parameters, conditions and materials without changing the scope or spirit of the invention or any embodiments thereof.

What is claimed is:

1. An immunoassay process for the detection of antigen in a sample, which comprises:
   a. forming a mixture of said sample in an appropriate medium therefor with
      1. a preformed antigen-binding complex of a primary antibody having specificity for said antigen and containing a F$_c$ region, and a secondary antibody having specificity only for F$_c$ region of said primary antibody; wherein said secondary antibody is affinity purified; and with
      2. A detectably labeled form of said antigen;
   b. incubating said mixture formed in step (a), which comprises said complex suspended in said medium, for a time sufficient to allow said antigen and said detectably labeled antigen to competitively bind to the primary antibody of said preformed complex;
   c. Separating said complex containing bound labeled antigen from said suspension medium; and
   d. detecting said separated complex containing bound labeled antigen, or said separated suspension medium containing free labeled antigen.

2. The process of claim 1 wherein said secondary binding macromolecule is an antibody.

3. The process of claims 1 or 2 wherein said preformed complex is free of any polymeric insoluble solid phase matrix.

4. The process of claim 1 wherein said primary antibody is present in an amount of 1–40 μg/ml.

5. The process of claim 4 wherein said primary antibody is present in an amount of 1–10 μg/ml.

6. The process of claim 1 wherein said preformed complex is free of non-specific IgG belonging to the same animal species as said primary antibody.

7. The process of claim 1 wherein said secondary binding macromolecule has been affinity purified by contact with an insoluble solid phase having F$_c$ fragments attached thereon.

8. The process of claim 2 wherein said antibody has been raised in an animal by immunizing said animal with F$_c$ fragments.

9. The process of claim 1 wherein said secondary binding macromolecule has been affinity purified by sequential contact with an insoluble solid phase having F$_c$ fragments attached thereon, and with another solid phase having human IgG attached thereon.

10. The process of claim 1 wherein said detectably labeled antigen is labeled with a radiolabel or an enzyme label.

11. The process of claim 1 wherein said antigen is T$_3$.

12. The process of claim 1 wherein said antigen is T$_4$.

13. The process of claim 1 wherein said antigen is digoxin.

14. An antigen-binding complex of an antigen-binding primary antibody containing a F$_c$ region unmodified, and a secondary unmodified antibody having specificity only for the F$_c$ region of the primary antibody, wherein said secondary antibody is affinity purified.

15. The complex of any of claims 14 which is free from any polymeric, insoluble solid phase matrix.

16. The complex of claim 14 which is free of non-specific IgG belonging to the same animal species as said antibody.

17. The complex of claim 14 wherein said secondary antibody has been affinity purified by contact with an insoluble solid phase having F$_c$ fragments attached thereon.

18. The complex of claim 14 wherein said second antibody has been raised in an animal by immunizing said animal with F$_c$ fragments.

19. The complex of claim 14 wherein said binding macromolecule has been affinity purified by sequential contact with an insoluble solid phase having F$_c$ fragments attached thereon, and with another solid phase having human IgG attached thereon.

20. A kit comprising a carrier being compartmentalized to receive at least two container means therein wherein the first of said container means comprises a preformed antigen binding complex of a primary antibody having specificity for said antigen, and having a $F_c$ region, and a secondary unmodified antibody having specificity only for the $F_c$ region of said primary antibody, wherein said secondary antibody is affinity purified, the second of said container means comprises a detectably labeled form of an antigen having affinity towards said primary antibody in said preformed complex.

21. The kit of claim 20 wherein said preformed complex in said first container means is dissolved in a buffer.

22. The kit of claim 20 wherein said detectably labeled antigen in said second container means is lyophilized.

23. The kit of claim 20 wherein said detectably labeled antigen in said second container means is dissolved in a buffer.

24. The kit of claim 20 which additionally contains a plurality of container means each comprising a mixture of said detectably labeled antigen and a non-labeled form of said antigen, each of said mixtures having a different molar ratio of detectably labeled to non-labeled antigen.

25. The kit of any of claims 20, 21, 22, 23, or 24 wherein said preformed complex in said first container means is free of any insoluble polymeric solid phase matrix.

26. The kit of any of claims 20, 21, 22, 23, or 24 wherein said preformed complex in said first container means is free of non-specific IgG belonging to the same animal species as said primary antibody.

27. The kit of any of claims 20, 21, 22, 23, or 24 wherein said secondary antibody has been purified by contact with an insoluble solid phase having $F_c$ fragments attached thereon.

28. The kit of any of claims 20, 21, 22, 23, or 24 wherein said detectably labeled antigen is $^{125}I$-$T_3$.

29. The kit of any of claims 20, 21, 22, 23, or 24 wherein said detectably labeled antigen is $^{125}I$-$T_4$.

30. The kit of any of claims 20, 21, 22, 23, or 24 wherein said detectably labeled antigen is $^{125}I$-digoxin.

31. The kit of claim 28 wherein said secondary antibody in said first container means has been rasied in an animal by immunizing said animal with $F_c$ fragments.

32. The kit of any of claims 20, 21, 22, 23, or 24 wherein said detectably labeled antigen is labeled with a radiolabel or an enzyme label.

33. A kit comprising a carrier being compartmentalized to receive at least one container means wherein said container means comprises (1) a preformed antigen-binding complex of a primary antibody having specificity for said antigen, and containing a $F_c$ region, secondary unmodified antibody having specificity only for the $F_c$ region of said primary antibody, wherein said secondary antibody is affinity purified, and (2) a predetermined amount of a detectably labeled form of an antigen having affinity towards the primary antibody in said complex.

34. An immunoassay process for the detection of Thyroxine Binding Globulin (TBG) in a sample, which comprises:

a. forming a mixture of said sample in an appropriate medium therefor with
   1. A preformed antigen-binding complex of
       a primary antibody, having specificity for $T_3$ and containing a $F_c$ region, and
       a secondary antibody having specificity only for the $F_c$ region of said primary antibody;
       wherein said secondary antibody is affinity purified; and with
   2. a detectably labeled form of $T_3$;
b. incubating said mixture formed in step (a), which comprises said complex suspended in said medium, for a time sufficient to allow said antigen and said detectably labeled $T_3$ to competitively bind to the primary antibody of said preformed complex and to said TBG in said sample;
c. separating said complex containing bound labeled $T_3$ from said suspension medium; and
d. detecting said separated complex containing bound labeled $T_3$, or said separated suspension medium containing labeled $T_3$ bound to TBG.

* * * * *